United States Patent [19]

Havera et al.

[11] 4,110,536
[45] Aug. 29, 1978

[54] DERIVATIVES OF 5-(INDOL-3-YL)HYDANTOIN

[75] Inventors: Herbert J. Havera, Edwardsburg, Mich.; Wallace G. Strycker, Goshen, Ind.

[73] Assignee: Miles Laboratories, Inc., Elkhart, Ind.

[21] Appl. No.: 788,154

[22] Filed: Apr. 18, 1977

[51] Int. Cl.$^2$ ............... C07D 413/14; A61K 31/535
[52] U.S. Cl. ............... 544/139; 260/293.61; 548/309; 424/248.54; 424/267; 424/273 R
[58] Field of Search ............... 544/139; 260/293.61

[56] References Cited

U.S. PATENT DOCUMENTS 3,560,495   2/1971   Frankus et al. ............... 260/293.63

*Primary Examiner*—Henry R. Jiles
*Assistant Examiner*—R. W. Ramsuer
*Attorney, Agent, or Firm*—Louis E. Davidson

[57] ABSTRACT

Derivatives of 5-(indol-3-yl)hydantoin characterized by the generic structural formula,

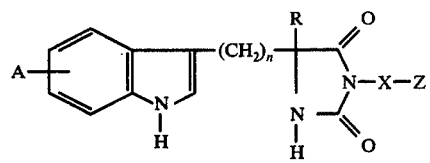

and their pharmacologically compatible salts are useful in the treatment of cardiac arrythmias in individuals for whom such therapy is indicated. In the preceding structural formula, A is a hydrogen atom, a halogeno, alkyl, hydroxyl, or an alkoxyl radical; $n$ is 0 or 1; R is a hydrogen atom or a phenyl group; X is a methylene, ethylene, trimethylene, or 2-hydroxytrimethylene radical; and Z is a monoalkylamino radical containing 1–4 carbon atoms, a dialkylamino radical containing 2–8 carbon atoms, a morpholino, piperid-1-yl, 4-phenyl-piperid-1-yl, or a 4-hydroxy-4-phenyl-piperid-1-yl radical.

21 Claims, No Drawings

DERIVATIVES OF 5-(INDOL-3-YL)HYDANTOIN

BACKGROUND OF THE INVENTION

1. Field of the Invention

Cardiac arrhythmias are disorders of impulse generation that result from disruptions of normal cardiac pacemaker activity, from disturbances in cardiac conductive fibers, or from a combination of both. Cardiac arrhythmias of clinical significance in man include: premature contractions (extrasystoles) originating in atrial or ventricular foci; paroxysmal supraventricular tachycardia; atrial flutter; atrial fibrillation; ventricular tachycardia; and ventricular fibrillation. Arrhythmias can be induced in laboratory animals that are suitable experimental models for man to study physiological mechanisms of the disorder or to screen new antiarrhythmic agents.

Clinical treatment of arrhythmias includes administration of a variety of drugs, although quinidine, procainamide, and diphenylhydantoin are current mainstays.

Quinidine is the d-isomer of quinine:

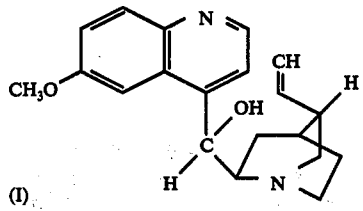

(I)

while procainamide is p-amino-N-(2-diethylaminoethyl)benzamide:

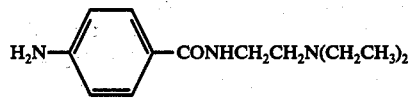

(II)

Quinidine and procainamide require extreme care in administration because they are relatively toxic. Because of limitations in those antiarrhythmic drugs, there have been efforts to discover safer substitutes. The discovery of the antiarrhythmic activity of diphenylhydantoin opened new approaches in the design of new compounds exhibiting such activity.

Diphenylhydantoin (5,5-diphenyl-2,4-imidazolidinedione; "DHP"),

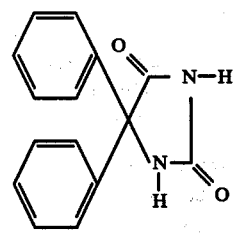

(III)

initially was utilized in the treatment of epilepsy but later was discovered to have important antiarrhythmic applications. The pharmacodynamics of DPH differ from those of quinidine and of procainamide. DPH specifically antagonizes ventricular arrhythmias induced by digitalis, depresses ventricular automaticity, enhances atrio-ventricular nodal conduction, and reduces the effective refractory period. DPH, however, is not without untoward side effects: dizziness, nausea, emesis, nystigmus, and ataxia. DPH is also toxic and may produce atrio-ventricular blockage, bradycardia, or even cardiac arrest accompanying its administration.

For a review of the current status of the field and of DPH as an antiarrhythmic agent, see: G. K. Moe and J. A. Albildskow, "Antiarrhythmic Drugs," in: *The Pharmacological Basis of Therapeutics*, 5th Edition, L. S. Goodman and A. Gilman, Editors, MacMillan Company, New York, Chapter 32 (1976); and L. S. Dreifus and Y. Watanabe, Amer. Heart J., 80: 709–713 (1970).

2. Description of the Prior Art

Six references report various syntheses of 5-(indol-3-yl)hydantoin,

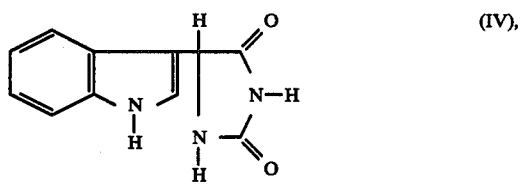

(IV), and describe the compound as useful in the preparation of tryptophan or other α-amino acids; none, however, discloses pharmacological utility of the compound. Those references include: Coker et al., J. Org. Chem., 27: 850 and 3209 (1962); published Japanese patent application No. 19,803/64 (1964); British Pat. Nos. 903,953 and 982,727 (1965); U.S. Pat. No. 3,419,551 (1968); and French Pat. No. 2,079,849 (1971).

Marchant and Harvey (J. Chem. Soc., 1808 [1951])provide details of the synthesis of 5- and 7-methoxytryptophan using 5-methoxyindol-3-yl and 5-[7-methoxyindol-3-yl]hydantoin intermediates respectively. The 5- and 7-methoxytryptophan derivatives are used in studies on tryptophan metabolism.

Finkbinder (J. Org. Chem., 30: 3414 [1965]) teaches use of 3-phenyl-5[(indol-3-yl)methyl]hydantoin in the preparation of trytophan and its analogues.

Published Japanese patent application No. 105716/72 (1974) reveals 5[(indol-3-yl)methyl]-5-methyl hydantoins having the structural formula,

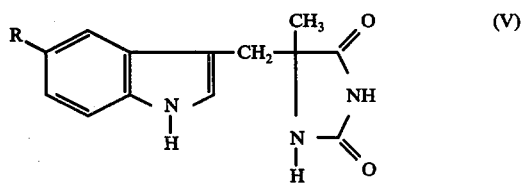

(V)

in which R is a hydrogen atom or a benzyloxy group. The patent discusses the utility of compounds V in terms of α-methyltryptophan precursors.

Sagetullin and Koronelli (Vestn. Mosk. Univ., Ser. II, Khim., 19: 68 [1964]) use 5-[(indol-3-yl)methylidene]-hydantoin as an intermediate in the synthesis of DL-abrine and 5-methoxyabrine.

U.S. Pat. No. 3,300,510 (1967) teaches that compounds characterized by the structure,

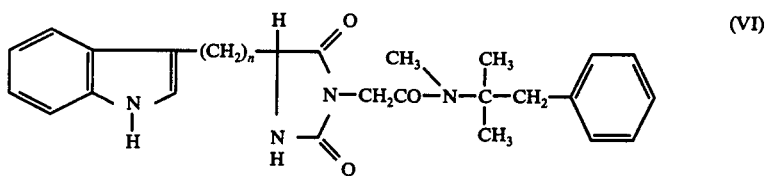

in which n is 1, 2, or 3, are mydriatic stimulants, analgesics, and antidepressants.

German Federal Republic Pat. No. 1,944,419 (1971) discloses that compounds having the formula,

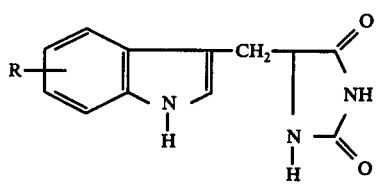

wherein R is an alkyl group containing 1-4 carbon atoms, or a benzyl group, have antiinflammatory properties.

From the preceding summary of the prior art, it is clear that the disclosed indolylhydantoins fall into two separate categories: (1) intermediates for the preparation of tryptophan and its analogues, which intermediates have no reported pharmacological activity; and (2) pharmacologically active agents of various utility. The latter category includes mydriatic stimulating, analgesic, antidepressant and antiinflammatory utilities but excludes antiarrhythmic utility. The prior art therefore provides no structure-activity relationships suggesting that indolylhydantoins may have antiarrhythmic properties.

SUMMARY OF THE INVENTION

The subject matter of this invention includes:
(1) pharmacologically active novel derivatives of 5-(indol-3-yl)hydantoin and their acid-addition salts;
(2) a method of preparing such derivatives;
(3) a therapeutic method of treating a cardiac arythmia in an individual for whom the method is indicated by administration of any such derivative or its pharmacologically compatible acid-addition salt; and
(4) a therapeutic method of treating a cardiac arrhythmia as described in (3), supra, by administration of prior art compounds: 5-(indol-3-yl)hydantoin, or 5-[(indol-3-yl)methyl]hydantoin.

DETAILED DESCRIPTION OF THE INVENTION

The derivatives of 5-(indol-3-yl)hydantoin that are part of the subject matter of this invention include compounds characterized by the general structural formula,

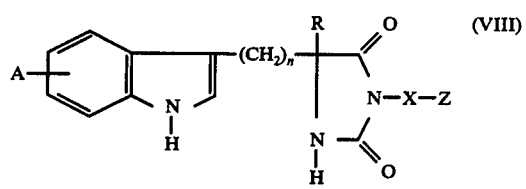

and their nontoxic, pharmacologically compatible acid-addition salts. In VIII, as well as in any other subsequent formula, A is a hydrogen atom, a halogeno (i.e., chloro, iodo, bromo, fluoro), hydroxyl, alkyl, or an alkoxyl radical, the latter two of which contains 1-4 carbon atoms; n is zero or one; R is a hydrogen atom or a phenyl radical; X is a methylene, ethylene, trimethylene, or a 2-hydroxytrimethylene radical; and Z is a moropholino, piperid-1-yl, 4-phenylpiperid-1-yl, 4-hydroxy-4-phenylpiperid-1-yl, a monoalkylamino radical containing 1-4 carbon atoms, or a dialkylamino radical containing 2-8 carbon atoms.

A preferred subgeneric class of VIII includes compounds having the structural formula,

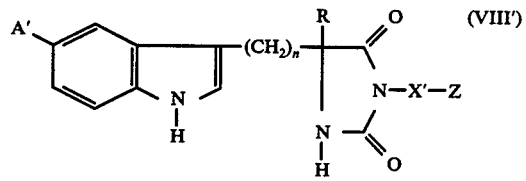

in which: A' is a hydrogen atom, a halogeno, or an alkoxyl radical containing 1-4 carbon atoms; and X' is a trimethylene or a 2-hydroxytrimethylene radical. Symbols A' and X' retain their respective meanings whenever they appear in any other subsequent structural formula.

Compounds VIII and VIII' and their pharmacologically compatible nontoxic salts are useful as cardiac antiarrhythmic agents. Example 22 provides details of such utility in reversing chloroform-induced arrhythmias in an experimental protocol recognized in the art (Lawson, J. Pharmacol. Exp. Therap., 160: 22 [1968]).

The method of preparing compounds VIII and VIII' proceeds via the one-step synthesis schematically diagrammed in TABLE A and described below.

TABLE A
SYNTHETIC PATHWAY FOR THE PREPARATION OF COMPOUND VIII

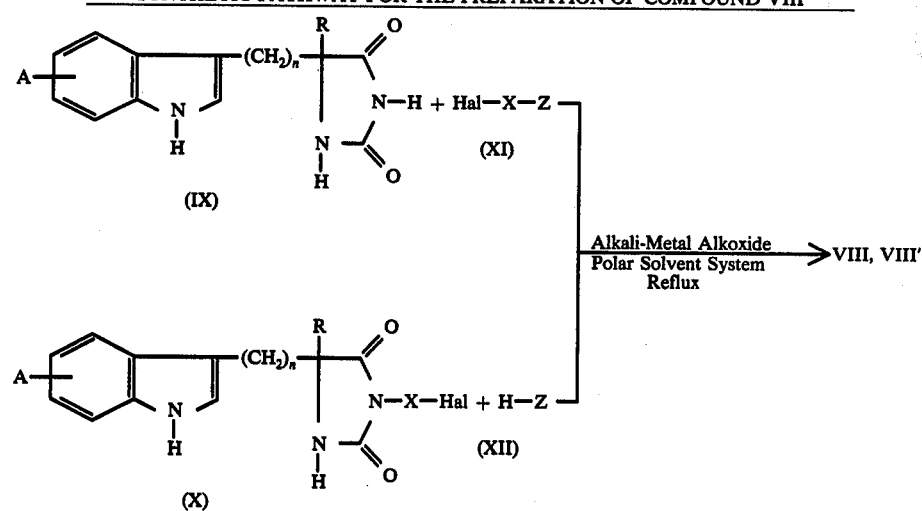

Reaction of an appropriate first starting material consisting of a 5-(indol-3-yl)hydantoin,

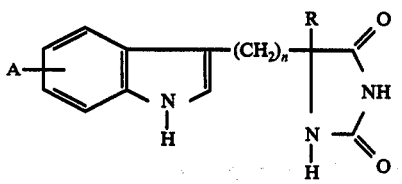

or a 3-(ω-halogenoalkyl)-5-(indol-3-yl)hydantoin,

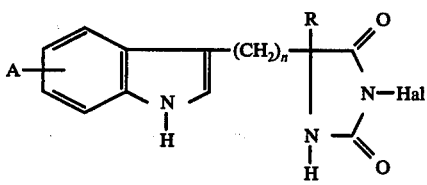

respectively with a selected second starting material comprising α-halogeno-ω-(substituted)alkane, Hal—X—Z    (XI)

or an amine,

H·Z    (XII), in a polar organic solvent, in the presence of an alkali-metal alkoxide, and under reflux for 1–20 hours provides the corresponding compound VIII. In formulas X and XI, the symbol, "Hal," means a chloro, bromo, or iodo substituent; "Hal" retains its definition hereafter in any structural formula.

A preferred mode of the method described above involves substitution of a first starting material having the formula,

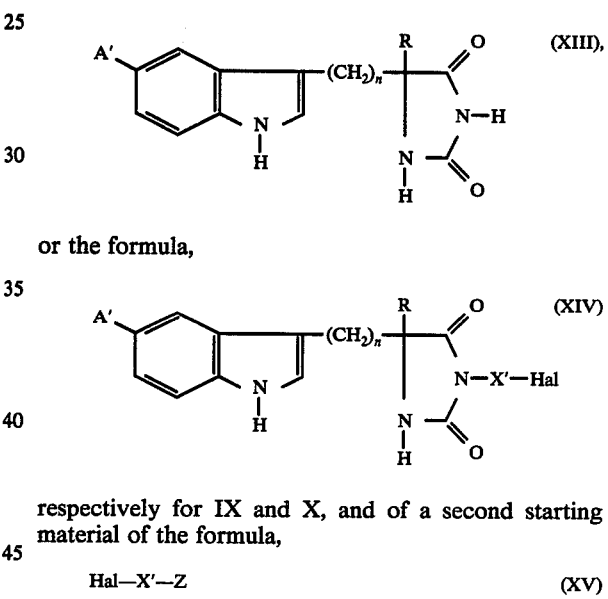

or the formula, respectively for IX and X, and of a second starting material of the formula, Hal—X′—Z    (XV)

for XI. Such preferred mode of the method provides corresponding compounds VIII′.

The solvent system used in the method is a polar solvent or a mixture of polar solvents. Examples include dimethylformamide, dimethylsulfoxide, methanol, ethanol, propanol or a mixture of any two of the preceding. Ethanol and formamide, especially a mixture of the two, represent preferred solvents.

Examples of the alkali-metal alkoxide used in the method include, but not exhaustively so, sodium, postassium, or lithium methoxide, ethoxide, propoxide (n- or sec-), or butoxide (n-, sec-, or tert).

The temperature of reaction depends upon the reflux temperature of the solvent system utilized.

First starting materials IX and XIII are prepared from appropriately substituted tryptophans according to methods reported in: Cohen et al., J. Org. Chem., 27: 850 and 2309 (1926); and published Japanese patent application No. 105716/72 (1974). Those methods include reaction of an appropriate tryptophan having the formula,

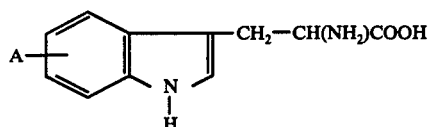
(XV),

Hal—(CH$_2$)$_m$—Hal  (XVII), in which m is an integer of the set 1–3, and the halogeno substituents are different. The pathway is provided in TABLE B.

TABLE B
PREPARATION OF 3-(Ω-HALOGENOALKYL)-5-(INDOL-3-YL)HYDANTOINS

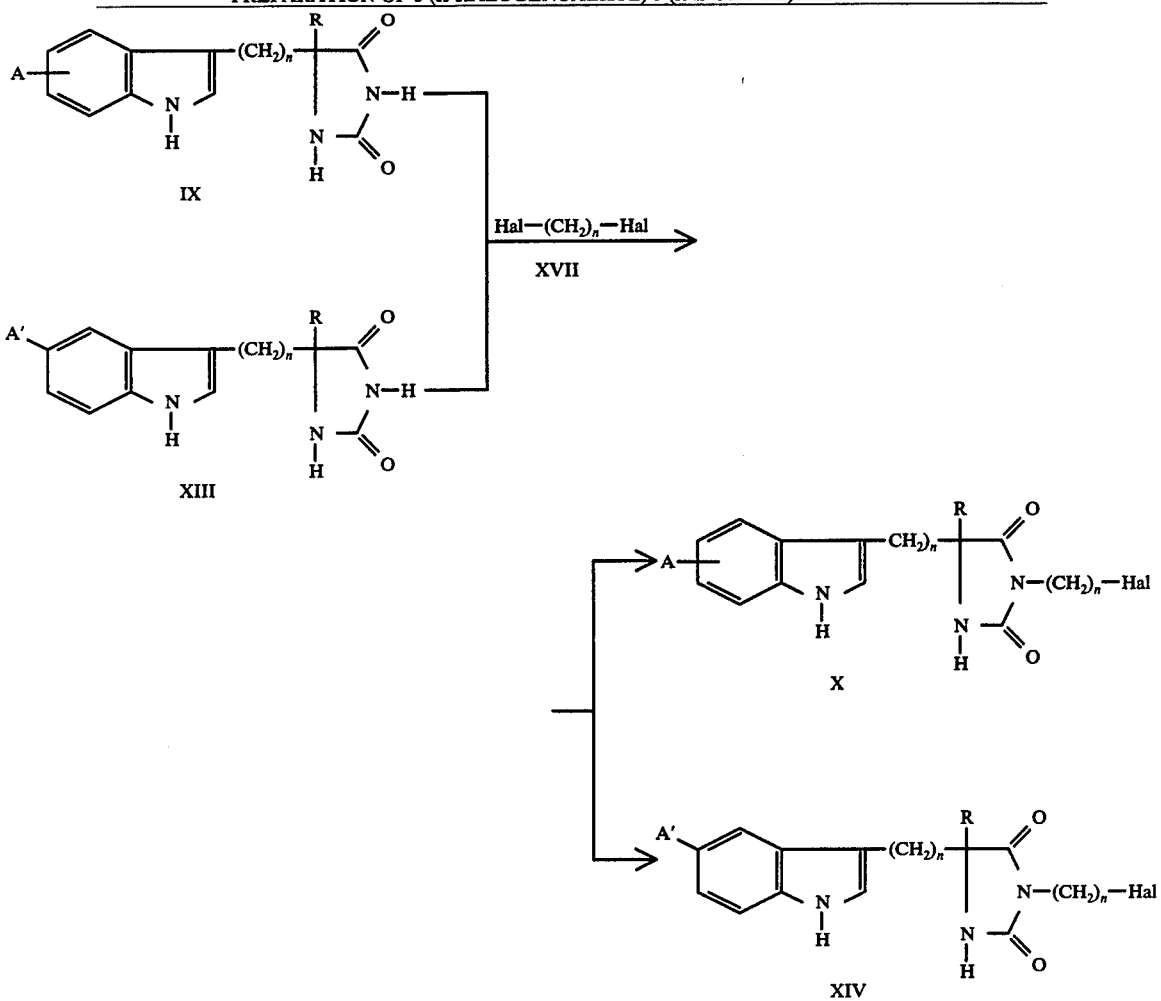

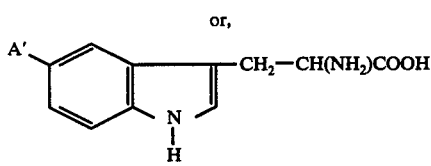
(XVI), with a cyanate ion source to obtain corresponding starting materials IX or XIII. Representative of the latter include: 5-(indol-3-yl)hydantoin, 5-(5-chloroindol-3-yl)hydantoin, 5-(5-methoxyindol-3-yl)hydantoin, 5-[(indol-3-yl)methyl]hydantoin, 5-[(5-chloroindol-3-yl)methyl]hydantoin, 5-[(5-methoxyindol-3-yl)methyl]hydantoin, 5-(indol-3yl)-5-phenylhydantoin.

First starting materials X and XIV in which X and X' are not a 2-hydroxytrimethylene radical respectively are prepared by reacting an appropriate compound IX or XIII with a selected α,ω-dihalogeno alkane having the formula, First starting materials X and XIV in which X and X' are 2-hydroxytrimethylene radicals are synthesized by reacting an appropriate compound IX or XIII with an epihalogenohydrin,

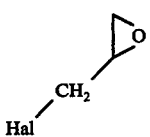
(XVIII)

to obtain corresponding materials X and XIV. TABLE C provides a schematic of synthesis.

Second starting materials XI in which X or X' is not a 2-hydroxytrimethylene radical are prepared by reacting an appropriate amine, XII, with a selected α,ω-dihalogenoalkene, XVII. In the case where X or X' is a 2-hydroxytrimethylene radical, compounds XI are obtained by reaction of an appropriate amine XII with an epihalogenohydrin, XVIII. TABLE D provides the reaction sequence.

Amines XII include morpholine, piperidine, 4-phenylpiperidine, 4-hydroxy-4-phenylpiperidine, alkylamines of 1–4 carbon atoms and dialkylamines of 2–8 carbon atoms.

Salts of compounds VIII and VIII' are prepared by conventional means by reaction with appropriate inorganic or organic acids such as: hydrochloric, maleic, oxalic, fumaric, and the like.

indicated. Such therapy comprises administering to such individual a therapeutically effective amount of a compound having structure IV, V (R=hydrogen), VIII, VIII' or a pharmacologically acceptable salt thereof. In the preceding sentence as elsewhere herein "individual" means a human being or a laboratory animal that is a suitable model for a human being, and "therapeutically effective amount" means a dose or series of doses that correct the arrhythmia to normal or near normal cardiac rhythm. The therapeutically effec-

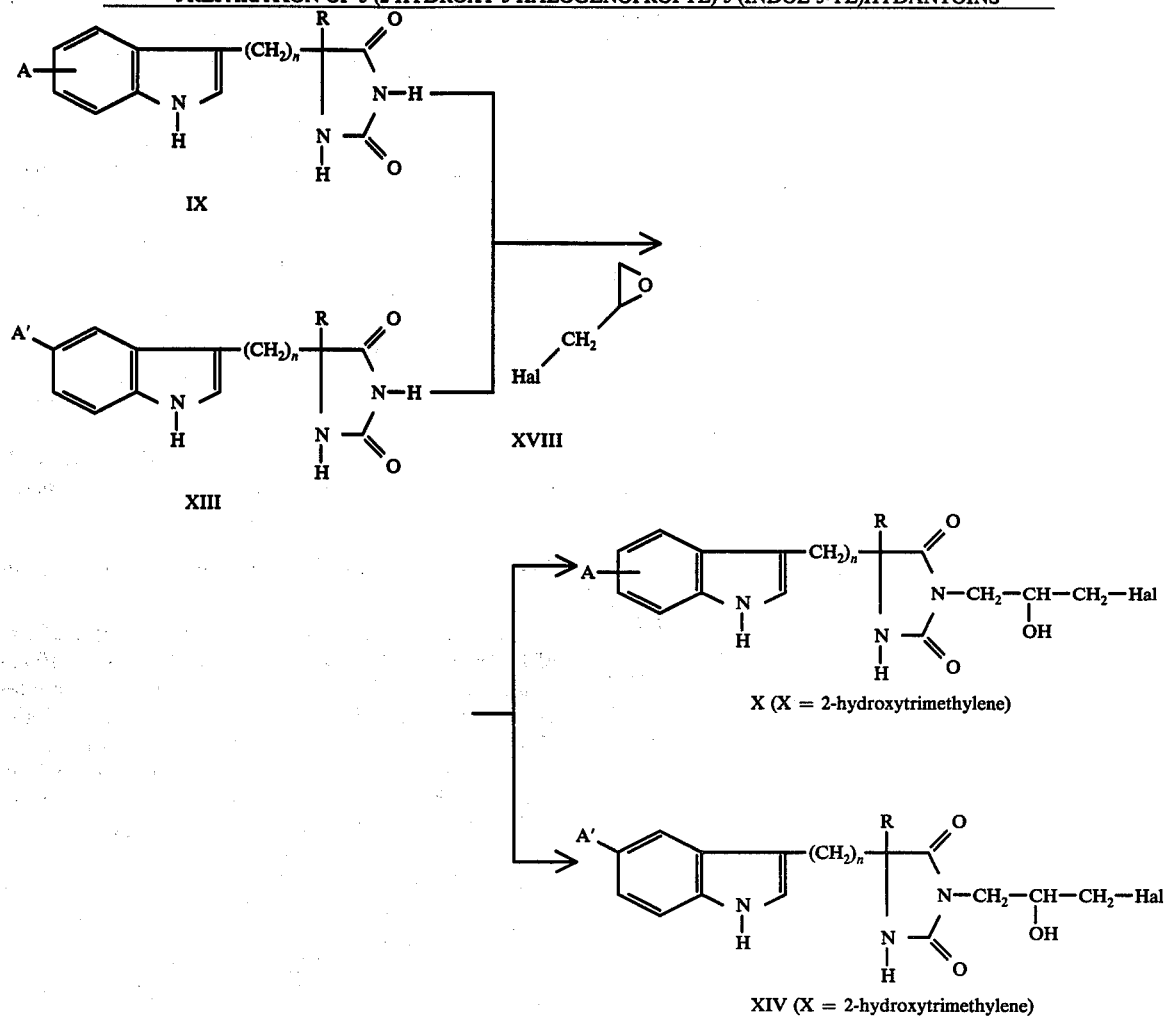

TABLE D
PREPARATION OF Ω-HALOGENOALKYLAMINES XI

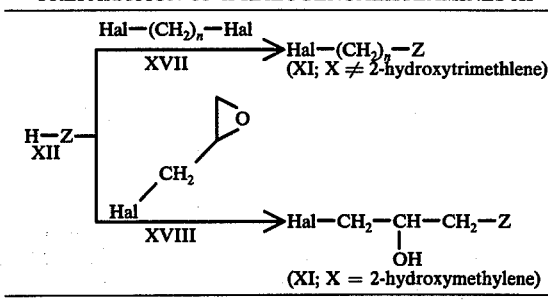

This invention also includes a method of chemotherapy of cardiac arrhythmias in whom that therapy is tive amount will vary from individual to individual and will depend upon the nature of the arrhythmia; but it is easily determined by one skilled in the art without undue experientation. Usually that amount may vary from 5 to 500 mg/day.

Forms suitable for administration are prepared by usual methods employed in the pharmaceutical arts for conventionally recognized modes of administration. Those modes of administration are oral, buccal, sublingual, rectal, parental, or intramuscular.

DESCRIPTION OF THE PREFERRED EMBODIMENTS

In the following examples: "DMF" is dimethylformamide; $NaOC_2H_5$ is sodium ethoxide; $C_2H_5OH$ is etha-

EXAMPLE 1

5-(Indol-3-yl)hydantoin

A mixture of indole-3-carboxaldehyde (43.6 g, 0.3 mole), KCN (29.3 g, 0.45 mole), $(NH_4)_2CO_3$ (144 g, 1.5 mole), 250 ml of $C_2H_5OH$, 250 ml of $H_2O$ and 200 ml of DMF was warmed with stirring at 70°–80° for 16 hours. The dark solution was filtered, cooled and acidified with concentrated HCl. The solid was collected, dissolved in dilute NaOH, filtered and acidified with dilute HCl. The solid was collected and recrystallized from aqueous methanol, yield 28.5 g, mp 229°–30°.

ANALYSIS— Calculated for $C_{11}H_9N_3O_2$: C, 61.40; H, 4.22; N, 19.52. Found: C, 61.75; H, 4.12; N, 19.92.

EXAMPLE 2

5-(Indol-3-yl)-5-phenylhydantoin

A mixture of 3-benzoylindole (22.1 g, 0.1 mole), KCN (7.2 g, 0.11 mole), $(NH_4)_2CO_3$ (28.8 g, 0.3 mole) and 200 ml of DMF was heated in a bomb at 110° for 42 hours. The mixture was diluted with NaOH, filtered to remove unreacted ketone and the filtrate was acidified with concentrated HCl with cooling. The solid was collected and recrystallized from aqueous $C_2H_5OH$ to yield 6.8 g of product, mp 302°–3°.

ANALYSIS— Calculated for $C_{17}H_{13}N_3O_2$: C, 70.10; H, 4.50; N, 14.43. Found: C, 70.31; H, 4.49; N, 14.26.

EXAMPLE 3

5-(5-Chloroindol-3-ylmethyl)hydantoin

A mixture of 5-chlorotryptophan (32 g, 0.14 mole) and potassium cyanate (22.6 g, 0.28 mole) in 500 ml of $H_2O$ was heated on the steam bath for 3 hours, cooled and acidified with concentrated HCl. The solid was collected, suspended in 500 ml of 10% HCl and heated on the steam bath for 2 hours. The solid, obtained on cooling, was dissolved in dilute NaOH, filtered and acidified with dilute HCl. The solid obtained was recrystallized from aqueous 2-PrOH. Yield 17 g (37.6%), m.p. 226°–8°, contains a mole of 2-PrOH.

ANALYSIS— Calculated for $C_{12}H_{10}ClN_3O_2 \cdot C_3H_8O$: C, 55.66; H, 5.61; N, 12.98. Found: C, 55.47; H, 5.13; N, 13.48.

EXAMPLE 4

1-(3-Chloropropyl)-4-hydroxy-4-phenylpiperidine

A solution of 4-hydroxy-4-phenylpiperidine (35.4 g, 0.2 mole) in 50 ml of 20% NaOH and 250 ml of acetone was cooled at <15° and 1-bromo-3-chloropropane (31.4 g, 0.2 mole) was added dropwise. The mixture was stirred at room temperature for 18 hours and concentrated in vacuo at <40°. The concentrate was converted to the HCl salt with HCL(g)/2-PrOH and concentrated in vacuo to an oil. The oil crystallized in hot acetone and the solid salt was collected and dried. The salt was warmed in 2-PrOH, cooled and filtered to remove 8 g of quaternary salt. mp >260°. The filtrate was warmed and diluted with ethyl acetate to obtain the desired salt. Yield 13 g (22.5%), m.p. 173°–6° (dec.).

ANALYSIS— Calculated for $C_{14}H_{20}ClNO \cdot HCl$: C, 57.92; H, 7.29; N, 4.82. Found: C, 57.44; H, 7.25; N, 4.60.

EXAMPLE 5

5-[(Indol-3-yl)methyl]-3-(3-morpholinopropyl)hydantoin

5-[(Indol-3-yl)methyl]hydantoin (5 g; 0.022 mole) was added to $NaOC_2H_5$ (0.022 mole) in 300 ml of anhydrous $C_2H_5OH$. The first mixture was heated to reflux, and 1-(3-chloropropyl)-morpholine (3.5 g, 0.022 mole) was added. The mixture was heated for 6 hours and then diluted with $H_2O$. The solid was collected and recrystallized from 2-propanol-petroleum ether, yield 3 g, mp 158°–60°.

ANALYSIS— Calculated for $C_{19}H_{25}ClN_4O_3$: C, 59.09; H, 6.41; N, 14.26. Found: C, 57.50; H, 6.46; N, 13.96.

EXAMPLE 6

5-(Indol-3-yl)-3-[3-(piperid-1-yl)propyl]hydantoin 5-(Indol-3-yl)hydantoin (8.6 g, 0.04 mole) in 200 ml of DMF was added to a solution of sodium (1.84 g, 0.08 mole) in 150 ml of anhydrous $C_2H_5OH$. N-(3-Chloropropyl)piperidine hydrochloride (7.9 g, 0.04 mole) was added and the mixture was heated to reflux with stirring for 18 hours, filtered and concentrated in vacuo to dryness. The concentrate was crystallized from aqueous methanol and twice recrystallized from aqueous DMF, yield 1.7 g, mp 233°–4° C.

ANALYSIS— Calculated for $C_{19}H_{24}N_4O_2$: C, 67.04; H, 7.11; N, 16.46. Found: C, 67.09; H, 6.72; N, 16.47.

EXAMPLE 7

5-(Indol-3-yl)-3-[3-(4-phenyl-1-piperidyl)propyl]hydantoin 5-(Indol-3-yl)hydantoin (7.5 g, 0.035 mole) in 200 ml of DMF was added to $NaOC_2H_5$ (0.070 mole) in 100 ml of anhydrous $C_2H_5OH$. After warming for 15 minutes, 1-(3-chloropropyl)-4-phenylpiperidine hydrochloride (9.6 g; 0.035 mole) was added and the mixture was heated to reflux with stirring for 8 hours, filtered and diluted with $H_2O$. The solid was collected and recrystallized from aqueous 2-propanol-DMF, yield 5 g, mp 245°–7° C.

ANALYSIS— Calculated for $C_{25}H_{28}N_4O_2$: C, 72.09; H, 6.77; N, 13.45. Found: C, 72.09; H, 6.67; N, 13.59.

The free base (5 g) was converted to the oxalate salt with oxalic acid in $CH_3OH$, recrystallized from hot aqueous DMF and again from 2-propanol-ethyl acetate, yield 1.8 g, mp 247°–248°.

ANALYSIS— Calculated for $C_{27}H_{30}N_4O_6$: C, 64.02; H, 5.97; N, 11.06. Found: C, 62.91; H, 5.95; N, 10.81.

EXAMPLE 8

5-(Indol-3-yl)-5-phenyl-3-[3-(1-piperidyl)propyl]hydantoin 5-(Indol-3-yl)-5-phenylhydantoin (2 g, 0.0069 mole) in 50 ml of DMF and 1-(3-chloropropyl)piperidine hydrochloride (1.36 g, 0.0069 mole) were added to $NaOC_2H_5$ (0.0138 mole) in 150 ml of anhydrous $C_2H_5OH$ and the mixture was heated to reflux with stirring for 8 hours. The mixture was filtered, diluted with $H_2O$ and the solid was collected and recrystallized from aqueous methanol, yield 2 g, mp 140°–2°.

ANALYSIS— Calculated for $C_{25}H_{27}N_4O_2$: C, 72.09; H, 6.77; N, 13.45. Found: C, 71.90; H, 7.10; N, 13.52.

The free base (2 g) was converted to the HCl salt and recrystallized from methanol-ether, yield 1.8 g, mp 274°–6°.

ANALYSIS— Calculated for $C_{25}H_{29}ClN_4O_2$: C, 66.29; H, 6.45; N, 12.37. Found: C, 66.73; H, 6.57; N, 12.51.

EXAMPLE 9

5-(Indol-3-ylmethyl)-3-[3-(4-phenyl-1-piperidyl)propyl]hydantoin

A mixture of 5-(indol-3-ylmethyl)hydantoin (6.4 g, 0.028 mole), 1-(3-chloropropyl)-4-phenylpiperidine (6.6 g, 0.028 mole) and 200 ml of DMF in 200 ml of anhydrous $C_2H_5OH$ and 0.028 mole of $NaOC_2H_5$ was heated under reflux with stirring for 10 hours. The mixture was filtered and the filtrate was diluted with $H_2O$. The solid was collected and twice recrystallized from aqueous $C_2H_5OH$, yield 2.0 g, mp 179°–80°.

ANALYSIS— Calculated for $C_{26}H_{30}N_4O_2$: C, 72.53; H, 7.02; N, 13.01. Found: C, 72.02; H, 7.06; N, 12.75.

EXAMPLE 10

5-(Indol-3-ylmethyl)-3-[3-(4-phenyl-1-piperidyl)propyl]hydantoin methiodide 5-(Indol-3-ylmethyl)-3-[3-(4-phenyl-1-piperidyl)propyl]hydantoin (5 g, 0.016 mole) was dissolved in 400 ml of hot ethyl acetate and iodomethane (2 g) was added. The mixture was heated under reflux for 1 hour and cooled. The solid was collected and recrystallized from methanol-ether, yield 3.2 g., mp 240°–1°.

ANALYSIS— Calculated for $C_{27}H_{33}IN_4O_2$: C, 56.65; H, 5.81; N, 9.78. Found: C, 56.36; H, 5.61; N, 9.44.

EXAMPLE 11

5-(5-Chloroindol-3-ylmethyl)-3-[3-(4-phenyl-1-piperidyl)propyl]hydantoin 5-(5-Chloroindol-3-ylmethyl)hydantoin (8 g, 0.025 mole) in 100 ml of DMF was added to $NaOC_2H_5$ (0.05 mole) in 200 ml of anhydrous $C_2H_5OH$ and after warming for 15 minutes, 1-(3-chloropropyl)-4-phenylpiperidine hydrochloride (6.8 g, 0.025 mole) was added. The mixture was heated to reflux with stirring for 8 hours, filtered and diluted with $H_2O$. The solid was collected and recrystallized from aqueous-DMF-methanol, yield 10 g, mp 222°–223°.

ANALYSIS— Calculated for $C_{26}H_{29}ClN_4O_2$: C, 67.16; H, 6.29; N, 12.05. Found: C, 67.22; H, 6.54; N, 12.68.

The free base (9 g) was converted to the hydrochloride and recrystallized from methanol and ethyl acetate, yield 6.5 g, mp 238°–40°.

ANALYSIS— Calculated for $C_{26}H_{30}Cl_2N_4O_2$: C, 62.27; H, 6.01; N, 11.17. Found: C, 62.68; H, 6.15; N, 11.15.

EXAMPLE 12

5-(Indol-3-yl)-5-phenyl-3-[3-(4-phenyl-1-piperidyl)propyl]hydantoin 5-(Indol-3-yl)-5-phenylhydantoin (6.5 g, 0.022 mole) in 100 ml of DMF was added to a solution of $NaOC_2H_5$ (0.044 mole) in 100 ml of anhydrous $C_2H_5OH$. After warming for 15 minutes, 1-(3-chloropropyl)-4-phenylpiperidine hydrochloride (6.1 g, 0.022 mole) was added and the mixture was heated to reflux with stirring for 18 hours, filtered and diluted with $H_2O$. The solid was collected, recrystallized from benzene and then from 2-propanol, yield 6.8 g, mp 176°–7°.

ANALYSIS— Calculated for $C_{31}H_{32}N_4O_2$: C, 75.59; H, 6.55; N, 11.37. Found: C, 75.95; H, 6.71; N, 11.40.

The free base (6.8 g) was converted to the maleate with maleic acid (3 g) in 2-propanol. The salt was recrystallized from methanol-2-propanol, yield 6.5 g, mp 195°–7°.

ANALYSIS— Calculated for $C_{35}H_{36}N_4O_6$: C, 69.06; H, 5.96; N, 9.20. Found: C, 68.66; H, 5.89; N, 9.05.

EXAMPLE 13

3-[3-(4-Hydroxy-4-phenylpiperid-1-yl)propyl]-5-[(indol-3-yl)methyl]hydantoin

A mixture of 5-[(indol-3-yl)methyl]hydantoin (5.1 g, 0.022 mole), 1-(3-chloropropyl)-4-hydroxy-4-phenylpiperidine hydrochloride (6.5 g, 0.022 mole), $NaOC_2H_5$ (0.044 mole) and 400 ml of anhydrous $C_2H_5OH$ was heated to reflux with stirring for 7 hours and poured into 1.5 l of cold $H_2O$. The solid was collected and recrystallized from aqueous methanol, yield 6.5 g, mp 176°–7°.

ANALYSIS— Calculated for $C_{26}H_{30}N_4O_3$: C, 69.94; H, 6.77; N, 12.54. Found: C, 69.28; H, 6.68; N, 12.38.

EXAMPLE 14

3-(3-Diethylaminopropyl)-5-(indol-3-yl)-5-phenylhydantoin

A solution of 5-(indol-3-yl)-5-phenylhydantoin (7.3 g, 0.025 mole) in 100 ml of DMF was added to a solution of sodium (1.15 g, 0.05 mole) in 100 ml of anhydrous ethanol. 3-Diethylaminopropyl chloride hydrochloride (4.6 g, 0.025 mole) was added and the mixture was heated to reflux with stirring for 16 hours, filtered and concentrated in vacuo to an oil. The oil was dissolved in chloroform, filtered and concentrated. The free base was crystallized from aqueous ethanol, yield 8.0 g, mp 100°.

ANALYSIS— Calculated for $C_{24}H_{28}N_4O_2$: C, 71.26; H, 6.98; N, 13.85. Found: C, 70.71; H, 7.28; N, 13.75.

The free base (8 g) was converted to the hydrochloride and recrystallized from methanol-ethyl acetate, yield 4.7 g, mp 262°–3°.

ANALYSIS— Calculated for $C_{24}H_{29}ClN_4O_2$: C, 65.52; H, 6.63; N, 12.70. Found: C, 64.57; H, 6.74; N, 12.50.

EXAMPLE 15

3-(3-Diethylaminopropyl)-5-(indol-3-yl)hydantoin

A solution of 5-(indol-3-yl)hydantoin (5.2 g, 0.024 mole) in 100 ml of DMF was added to a solution of sodium (1.1 g) in 100 ml of anhydrous $C_2H_5OH$. The solution was warmed 3-diethylaminopropyl chloride hydrochloride (4.5 g, 0.024 mole) was added and the mixture was heated to reflux with stirring for 18 hours, filtered and diluted with $H_2O$. The crude free base (2.5 g) and oxalic acid (1.5 g) was dissolved in methanol and diluted with ethyl acetate. The solid was collected and dried, yield 1.0 g, mp 231°–2°.

ANALYSIS— Calculated for $C_{20}H_{26}N_4O_6$: C, 57.40; H, 6.27; N, 13.40. Found: C, 56.80; H, 6.01; N, 13.26.

EXAMPLE 16

3-(3-Diethylaminopropyl)-5-(indol-3-ylmethyl)hydantoin

A mixture of 5-(indol-3-ylmethyl)hydantoin (10 g, 0.04 mole), 3-chloro-N,N-diethylpropylamine hydrochloride (8.2 g, 0.04 mole), $NaOC_2H_5$ (0.08 mole) and 500 ml of anhydrous $C_2H_5OH$ was heated to reflux with stirring for 20 hours. The mixture was filtered and concentrated to dryness. The concentrate was dissolved in $CHCl_3$, filtered and concentrated. The concentrate was crystallized and recrystallized from benzene-petroleum ether. The solid was again recrystallized from xylene and the solvated solid was dried in vacuum, yield 2.5 g, mp 90°.

ANALYSIS— Calculated for $C_{19}H_{26}N_4O_2$: C, 66.64; H, 7.65; N, 16.36. Found: C, 66.04; H, 7.62; N, 15.99.

EXAMPLE 17

5-(5-Chloroindol-3-ylmethyl)-3-(diethylaminopropyl)hydantoin 5-(5-Chloroindol-3-ylmethyl)hydantoin (5 g, 0.019 mole) was added to a solution of sodium (0.88 g) in 200 ml of anhydrous $C_2H_5OH$. After heating to reflux for 30 minutes, 3-diethylaminopropyl chloride hydrochloride (3.54 g, 0.019 mole) was added and the mixture was heated to reflux with stirring for 18 hours. The mixture was filtered and diluted with $H_2O$ to form a solid. The solid was recrystallized from aqueous 2-propanol, twice from acetone-petroleum ether and again from 2-propanol, yield 1.8 g, mp 186°.

ANALYSIS— Calculated for $C_{19}H_{25}ClN_4O_2$: C, 60.55; H, 6.95; N, 14.90. Found: C, 60.64; H, 6.63; N, 14.95.

EXAMPLE 18

3-(3-Diethylaminopropyl)-5-(5-methoxyindol-3-ylmethyl)hydantoin

3-Diethylaminopropyl chloride hydrochloride (3.75 g, 0.024 mole) and a solution of 5-(5-methoxyindol-3-ylmethyl)hydantoin (6.1 g, 0.024 mole) in 100 ml of DMF were added to a solution of sodium (1.1 g) in 200 ml of anhydrous ethanol and the mixture was heated to reflux with stirring for 8 hours, filtered and concentrated in vacuo. The residue was recrystallized from aqueous methanol, yield 1.8 g, mp 136°.

ANALYSIS— Calculated for $C_{20}H_{28}N_4O_3$: C, 64.49; H, 7.58; N, 15.04. Found: C, 64.16; H, 7.60; N, 14.76.

EXAMPLE 19

3-(3-t-Butylamino-2-hydroxypropyl)-5-(indol-3-ylmethyl)hydantoin

A mixture of 5-(indol-3-ylmethyl)hydantoin (11.5 g, 0.05 mole) in $NaOC_2H_5$ (0.05 mole) and 300 ml of anhydrous $C_2H_5OH$ was heated to reflux and 20 g of epichlorohydrin were added. The mixture was heated to reflux for 7 hours, filtered and concentrated in vacuo to an oil. The concentrate and t-butylamine (10 ml) in 100 ml of anhydrous $C_2H_5OH$ were heated to reflux for 3 hours and concentrated in vacuo. The free base crystallized in ether and was recrystallized from 2-propanol-petroleum ether. The solid was twice recrystallized from 2-propanol and again from acetone-petroleum ether, yield 2.5 g, mp 190°-1°.

ANALYSIS— Calculated for $C_{19}H_{26}N_4O_3$: C, 63.38; H, 7.31; N, 15.63. Found: C, 63.82; H, 7.29; N, 15.59.

EXAMPLE 20

5-(Indol-3-ylmethyl)-3-(3-piperidylpropyl)hydantoin

A mixture of 5-(indol-3-ylmethyl)hydantoin (10 g, 0.043 mole), N-(3-chloropropyl)piperidine hydrochloride (8.6 g, 0.043 mole), $NaOC_2H_5$ (0.086 mole), 350 ml of anhydrous $C_2H_5OH$ and 100 ml DMF was heated to reflux with stirring for 6 hours and poured into 1.5 l of $H_2O$. The solid was collected and recrystallized from aqueous methanol, yield 11.7 g, mp 185°.

ANALYSIS— Calculated for $C_{20}H_{26}N_4O_2$: C, 67.78; H, 7.39; N, 15.81. Found: C, 67.45; H, 7.32; N, 15.64.

The free base (3.5 g) was converted to the oxalate with oxalic acid (1 g) in $CH_3OH$-ethyl acetate and recrystallized from 2-propanol-methanol-ether, yield 1.9 g, mp 184°-5°.

ANALYSIS— Calculated for $C_{22}H_{28}N_4O_6$: C, 59.45; H, 6.35; N, 12.61. Found: C, 60.05; H, 6.54; N, 12.64.

EXAMPLE 21

5-(5-Methoxyindol-3-ylmethyl)-3-[3-(4-phenylpiperid-1-yl)propyl]hydantoin

A mixture of 5-(5-methoxyindol-3-ylmethyl)hydantoin (5.5 g, 0.21 mole), 1-(3-chloropropyl)-4-phenylpiperidine hydrochloride (5.8 g, 0.021 mole), $NaOC_2H_5$ (0.042 mole) in 200 ml of anhydrous $C_2H_5OH$ was heated to reflux with stirring for 18 hours, filtered and concentrated in vacuo to dryness. The solid was recrystallized from aqueous methanol, yield 7.9 g, mp 176°-7°.

ANALYSIS— Calculated for $C_{27}H_{32}N_4O_3$: C, 70.41; H, 7.00; N, 12.16. Found: C, 68.37; H, 6.92; N, 12.29.

The free base (7.5 g, 0.016 mole) was converted to the oxalate with oxalic acid (4 g) in acetone and the salt was recrystallized from ethanol-methanol-ethyl acetate, yield 6.5 g, 182°-4°.

ANALYSIS— Calculated for $C_{29}H_{34}N_4O_7$: C, 63.27; H, 6.22; N, 10.18; O, 20.34. Found: C, 63.17; H, 6.33; N, 10.09; O, 20.51.

EXAMPLE 22

Antiarrhythmic Activity

The antiarrhythmic activity of the compounds listed above were tested in the experimental model reported by J. W. Lawson (J. Pharmacol. Exp. Therap., 160: 22–31 (1968).

The test compounds were administered in varying intraperitoneal doses to groups consisting of 5 mice. Ten minutes after administration of a given dose of a compound, a mouse was transferred to a covered 300 ml glass beaker that contained a wad of cotton saturated with about 20 ml of chloroform. The animal was observed closely and removed from the beaker immediately after respiratory arrest. The heart was quickly exposed by making an incision through the abdomen, diaphragm, thorax and pericardium for visual inspection of ventricular rate and rhythm. Ventricular contractions were counted for 30 seconds. According to the procedure reported by Lawson, animals with ventricular rate not exceeding 100 contractions during the 30 second observation period were considered protected. Results obtained with each dose were used to calculate the mean effective doses ($ED_{50}$) and 95% confidence limits (95% CL) after the method of Litchfield and Wilcoxin (J. Pharmacol. Exp. Therap., 96: 99–113 [1949]).

LD$_{50}$ data were obtained by standard procedures known to the art.

In order to obtain an indication of the specificity and/or safety margin of the antiarrhythmic effect, the acute toxicity of the compounds was investigated. This was carried out by administering log-spaced intraperitoneal doses of the test compounds to groups of five mice. Death was scored within a period of 48 hours after dosing and the LD$_{50}$ and 95% confidence limits calculated as described above. The therapeutic index of each compound (LD$_{50}$.ED$_{50}$) was taken derived from the corresponding data.

In TABLE E, the compounds of this invention are listed by their example number and the prior art compounds by their assigned Roman numeral. TABLE E demonstrates the nonobvious nature of the claimed compounds and the technical advance thereof over DPH.

TABLE C

| Antiarrhythmic Activity and Therapeutic Index of Indolylhydantoin Derivatives in the Mouse | | | |
|---|---|---|---|
| Example No. | ED$_{50}$ (95% C.L.) mg/kg, i.p. | LD$_{50}$ (95% C.L.) mg/kg, i.p. | Therapeutic Index |
| 6 | 21 (11–39 | 66 (49–87) | 3.1 |
| 9 | 7.5 (4–16) | 19 (12–31) | 2.5 |
| 10 | 19.6 (11–35) | 69 | 3.5 |
| 11 | 37 (26–53) | 69 | 1.9 |
| 12 | 80 (85–118) | 63 | 0.9 |
| 13 | 23.0 (13–43) | 57 (28–114) | 2.5 |
| 14 | 27 (19–38) | 48 | 1.8 |
| 15 | 44 (24–81) | 79 (57–109) | 1.8 |
| 17 | 44 (23–81) | 74 | 1.7 |
| 18 | 13 (7–25) | 61 | 4.7 |
| 20 | 23.8 (12–45) | 190 (157–241) | 8.0 |
| 21 | 9 (5–17) | 24 (18–34) | 2.7 |
| III | 123 (69–170) | 95 (73–123) | 0.8 |
| V (R=II) | 72 | 307 (196–482) | 4.3 |

What is claimed is:

1. A compound having the formula,

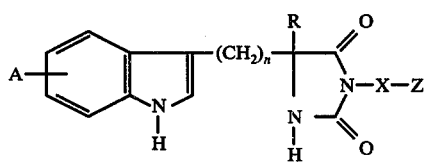

or a nontoxic, pharmacologically compatible salt thereof, in which:

A is a hydrogen atom, a halogeno, a hydroxyl, an alkyl, or an alkoxyl radical, the latter two of which contain 1–4 carbon atoms;

n is 0 or 1;

R is a hydrogen atom or a phenyl radical;

X is a methylene, ethylene, trimethylene, or 2-hydroxytrimethylene radical; and

Z is a morpholino, piperid-1-yl, 4-phenylpiperid-1-yl or 4-hydroxy-4-phenylpiperid-1-yl.

2. A compound having the formula,

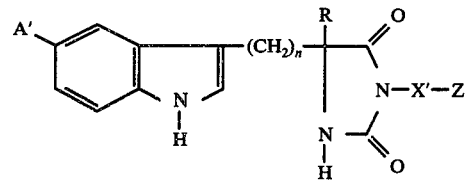

or a nontoxic, pharmacologically compatible salt thereof, in which:

A' is a hydrogen atom, a halogeno or an alkoxyl radical containing 1–4 carbon atoms;

n is 0 or 1;

R is a hydrogen atom or a phenyl radical;

X' is a trimethylene or a 2-hydroxy-trimethylene radical; and

Z is a morpholino, piperid-1-yl, 4-phenylpiperid-1-yl or 4-hydroxy-4-phenylpiperid-1-yl.

3. The compound as in claim 1, 5-[(indol-3-yl)methyl]-3-[(3-morpholino)propyl]hydantoin.

4. The compound as in claim 1, 5-[indol-3-yl)methyl]-3-[(3-morpholino)propyl]hydantoin hydrochloride.

5. The compound as in claim 1, 5-(indol-3-yl)-3-[3-piperid-1-yl)propyl]hydantoin.

6. The compound as in claim 1, 5-(indol-3-yl)-5-phenyl-3-[3-(piperid-1-yl)-propyl]hydantoin.

7. The compound as in claim 1, 5-(indol-3-yl)-5-phenyl-3-[3-(piperid-1-yl)-propyl]hydantoin hydrochloride.

8. The compound as in claim 1, 5-(indol-3-yl)-3-[(4-phenylpiperid-1-yl)propyl]hydantoin.

9. The compound as in claim 1, 5-(indol-3-yl)-3-[(4-phenylpiperid-1-yl)propyl]hydantoin oxalate.

10. The compound as in claim 1, 3-[3-(4-phenylpiperid-1-yl)propyl]-5-[(indol-3-yl)methyl]hydantoin.

11. The compound as in claim 1, 3-[3-(4-phenylpiperid-1-yl)propyl]-5-[(indol-3-yl)methyl]hydantoin methiodide.

12. The compound as in claim 1, 5-[(5-chloroindol-3-yl)methyl]-3-[3-(4-phenylpiperid-1-yl)propyl]hydantoin.

13. The compound as in claim 1, 5-[(5-chloroindol-3-yl)methyl]-3-[3-(4-phenylpiperid-1-yl)propyl]hydantoin hydrochloride.

14. The compound as in claim 1, 5-[(5-methoxyindol-3-yl)methyl]-3-[3-(4-phenylpiperid-1-yl)propyl]hydantoin.

15. The compound as in claim 1, 5-[(5-methoxyindol-3-yl)methyl]-3-[3-(4-phenylpiperid-1-yl)propyl]hydantoin oxalate.

16. The compound as in claim 1, 5-(indol-3-yl)-5-phenyl-3-[3-(4-phenylpiperid-1-yl)propyl]hydantoin.

17. The compound as in claim 1, 5-(indol-3-yl)-5-phenyl-3-[3-(4-phenylpiperid-1-yl)propyl]hydantoin maleate.

18. The compound as in claim 1, 3-[3-(4-hydroxy-4-phenylpiperid-1-yl)propyl]-5-[(indol-3-yl)methyl]hydantoin.

19. The compound as in claim 1, 3-[3-(4-hydroxy-4-phenylpiperid-1-yl)propyl]-5-[(indol-3-yl)methyl]hydantoin oxalate.

20. 5-[(Indol-3-yl)methyl]-3-[3-(piperid-1-yl)propyl]hydantoin.

21. 5-[Indol-3-yl)methyl]-3-[3-(piperid-1-yl)propyl]hydantoin oxalate.

* * * * *